(12) United States Patent
Ito

(10) Patent No.: US 11,615,796 B2
(45) Date of Patent: Mar. 28, 2023

(54) INFORMATION PROCESSING APPARATUS, INFORMATION PROCESSING SYSTEM, AND INFORMATION PROCESSING METHOD

(71) Applicant: Tatsuo Ito, Kanagawa (JP)

(72) Inventor: Tatsuo Ito, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 239 days.

(21) Appl. No.: 17/078,286

(22) Filed: Oct. 23, 2020

(65) Prior Publication Data

US 2021/0134289 A1    May 6, 2021

(30) Foreign Application Priority Data

Oct. 31, 2019   (JP) .............................. JP2019-198952

(51) Int. Cl.
| | | |
|---|---|---|
| G10L 15/00 | (2013.01) | |
| G10L 15/22 | (2006.01) | |
| G06Q 10/0631 | (2023.01) | |
| G10L 15/26 | (2006.01) | |
| G06F 3/14 | (2006.01) | |

(52) U.S. Cl.
CPC ................ *G10L 15/22* (2013.01); *G06F 3/14* (2013.01); *G06Q 10/0631* (2013.01); *G10L 15/26* (2013.01)

(58) Field of Classification Search
CPC .......... G10L 15/22; G06F 3/167; G16H 10/60
See application file for complete search history.

(56) References Cited

U.S. PATENT DOCUMENTS

| | | | | |
|---|---|---|---|---|
| 10,403,393 | B2* | 9/2019 | Gifford ................... | G16H 10/60 |
| 11,033,239 | B2* | 6/2021 | Cheenepalli ............. | G11B 3/00 |
| 11,094,322 | B2* | 8/2021 | Lavery ................... | G16H 50/50 |
| 11,120,217 | B2* | 9/2021 | Maes ..................... | G06F 9/5038 |
| 11,222,716 | B2* | 1/2022 | Vozila .................... | G06F 3/167 |
| 2009/0216534 | A1* | 8/2009 | Somasundaram ..... | G16H 40/20 |
| | | | | 705/28 |
| 2015/0294089 | A1* | 10/2015 | Nichols ................... | G06F 3/167 |
| | | | | 705/3 |
| 2020/0152190 | A1* | 5/2020 | Itkowitz ................. | A61B 34/76 |

FOREIGN PATENT DOCUMENTS

| | | |
|---|---|---|
| JP | 62-042200 | 2/1987 |
| JP | 2005-251041 | 9/2005 |
| JP | 2008-123191 | 5/2008 |
| JP | 2016-053804 | 4/2016 |
| JP | 2017-122965 | 7/2017 |
| JP | 2018-045646 | 3/2018 |
| JP | 2018-045647 | 3/2018 |
| WO | WO2018/164165 A1 | 9/2018 |

* cited by examiner

*Primary Examiner* — Daniel Abebe
(74) *Attorney, Agent, or Firm* — IPUSA, PLLC

(57) ABSTRACT

An information processing apparatus, an information processing system, and an information processing method. The information processing apparatus identifies a work target and work content of work, based on voice data sent from a terminal for inputting utterance about the work by a worker, updates work implementation status information indicating work implementation status of the work stored in a memory based on the work target and work content of the work that are identified, and controls to display the work implementation status of the work based on the work implementation status information on a display terminal connected through a network.

14 Claims, 17 Drawing Sheets

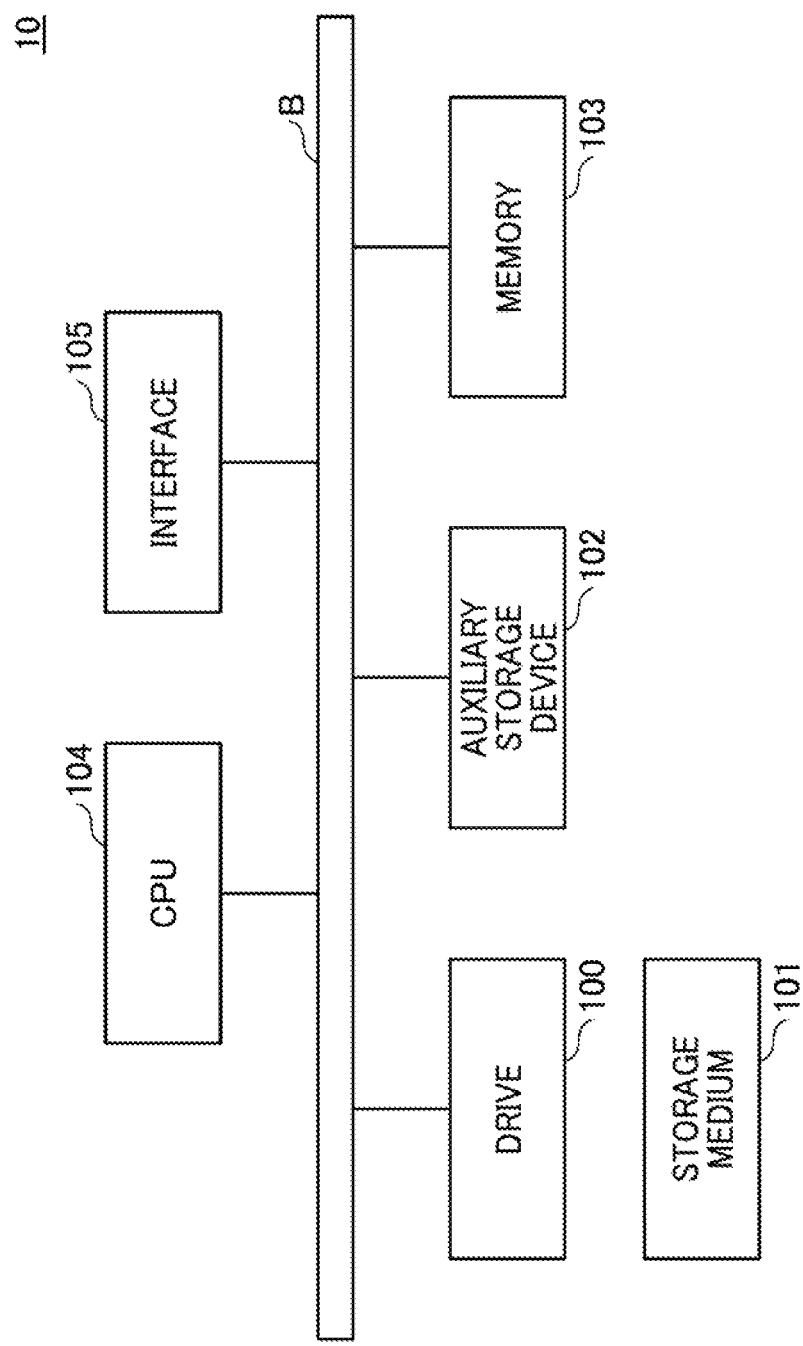

| STAFF ID | MESSAGE USER ID |
|---|---|
| User01 | aaa |
| User02 | bbb |
| User03 | ccc |
| ... | ... |

| VOICE RECORD ID | STAFF ID | VOICE URL | TEXT DATA |
|---|---|---|---|
| 0001 | User02 | https://aaa/0001.wav | ROOM 102 MR. B SEATING |
| 0002 | User01 | https://aaa/0002.wav | ROOM 101 MR. A SEATING |
| 0003 | User01 | https://aaa/0003.wav | ROOM 102 MR. B STARTS MEAL |
| 0004 | User01 | https://aaa/0004.wav | |

(PREPRANDIAL MEDICATION) [RESIDENT ID] (IDENTITY CONFIRMATION) [WORK RESULT]

[ROOM]<NUMBER>[MR./MS.]<NAME>

[COMPLETED/OK/FINISHED]

FIG. 8

| VOICE RECORD ID | STAFF ID | VOICE URL | TEXT DATA |
|---|---|---|---|
| 0001 | User02 | https://aaa/0001.wav | ROOM 102 MR. B SEATING |
| 0002 | User01 | https://aaa/0002.wav | ROOM 101 MR. A SEATING |
| 0003 | User01 | https://aaa/0003.wav | ROOM 102 MR. B STARTS MEAL |
| 0004 | User01 | https://aaa/0004.wav | PREPRANDIAL MEDICATION ROOM 101 MR. A IDENTITY CONFIRMATION OK |

| WORK ITEM | RESIDENT ID | WORK SUB ITEM | WORK RESULT |
|---|---|---|---|
| PREPRANDIAL MEDICATION | MR. A ROOM 101 | IDENTITY CONFIRMATION | OK |

FIG. 11

| | SCHEDULE INFORMATION | | | WORK IMPLEMENTATION STATUS INFORMATION | | | |
|---|---|---|---|---|---|---|---|
| RESIDENT ID | DATE | WORK ITEM | WORK SUB ITEM | WORK RESULT | STAFF ID | VOICE RECORD ID | |
| ROOM 101 MR. A | 10072019 | SEATING | - | 07:05 | User01 | 0002 | |
| ROOM 101 MR. A | 10072019 | PREPRANDIAL MEDICATION | IDENTITY CONFIRMATION | 07:10 | User02 | 0004 | |
| ROOM 101 MR. A | 10072019 | PREPRANDIAL MEDICATION | MEDICATION CONFIRMATION | 07:10 | User02 | 0005 | |
| ROOM 101 MR. A | 10072019 | PREPRANDIAL MEDICATION | SWALLOW CONFIRMATION | 07:11 | User02 | 0006 | |
| ROOM 101 MR. A | 10072019 | MEAL | START | 07:15 | User01 | 0007 | |
| ROOM 101 MR. A | 10072019 | MEAL | COMPLETE | | | | |
| ... | ... | ... | ... | ... | ... | ... | |
| ROOM 102 MR. B | 10072019 | SEATING | - | 07:03 | User02 | 0001 | |
| ROOM 102 MR. B | 10072019 | MEAL | START | 07:05 | User01 | 0003 | |
| ROOM 102 MR. B | 10072019 | MEAL | COMPLETE | 07:30 | User01 | 0008 | |
| ROOM 102 MR. B | 10072019 | POSTPRANDIAL MEDICATION | IDENTITY CONFIRMATION | | | | |
| ... | ... | ... | ... | ... | ... | ... | |

FIG. 12

| NO | RESIDENT | | ABSENT | SEATING | PREPRANDIAL MEDICATION | | | MEAL | | POSTPRANDIAL MEDICATION | BATHING | ... |
|---|---|---|---|---|---|---|---|---|---|---|---|---|
| | ROOM NO. | NAME | | | PERSONAL IDENTIFI-CATION | MEDICA-TION CONFIR-MATION | SWALLOW CONFIR-MATION | START | COM-PLETE | | | |
| 1 | 101 | A | | 7:05 User01 | 7:10 User02 | 7:10 User02 | 7:11 User02 | 7:15 User01 | | | | |
| 2 | 102 | B | | 7:03 User02 | | | | 7:05 User01 | 7:30 User01 | | | |
| 8 | 105 | E | | | | | | | | | | |

| WORK ITEM | WORK SUB ITEM |
|---|---|
| SEATING | – |
| PREPRANDIAL MEDICATION | IDENTITY CONFIRMATION |
| | MEDICATION CONFIRMATION |
| | SWALLOW CONFIRMATION |
| MEAL | START |
| | COMPLETE |
| BATHING | START |
| | COMPLETE |
| ⋮ | ⋮ |

FIG. 14

ROOM 102 MR. B
STARTS MEAL

VOICE DATA:
https://aaa/0003.wav

ROOM 101 MR. A
PREPRANDIAL MEDICATION
IDENTITY CONFIRMATION OK

VOICE DATA:
https://aaa/0004.wav

| WORK ITEM TO MONITOR | WORK SUB ITEM TO MONITOR | REFERENCE WORK ITEM | REFERENCE WORK SUB ITEM | ALLOWABLE TIME |
|---|---|---|---|---|
| POSTPRANDIAL MEDICATION | — | MEAL | COMPLETE | 30 MINUTES |
| : | : | : | : | : |

T1

INFORMATION PROCESSING APPARATUS, INFORMATION PROCESSING SYSTEM, AND INFORMATION PROCESSING METHOD

CROSS-REFERENCE TO RELATED APPLICATIONS

This patent application is based on and claims priority pursuant to 35 U.S.C. § 119(a) to Japanese Patent Application No. 2019-198952, filed on Oct. 31, 2019, in the Japan Patent Office, the entire disclosure of which is hereby incorporated by reference herein.

BACKGROUND

Technical Field

The present disclosure relates to an information processing apparatus, an information processing system, and an information processing method.

Background Art

In a nursing facility, one or more staff members who are in charge of one or more care recipients perform various operations. In this case, it is important that work (for example, medication, meals, etc.) is performed on the care recipients appropriately to prevent duplicated work and to prevent mistakes such as omission of work execution.

SUMMARY

Embodiments of the present disclosure describe an information processing apparatus, an information processing system, and an information processing method. The information processing apparatus identifies a work target and work content of work, based on voice data sent from a terminal for inputting utterance about the work by a worker, updates work implementation status information indicating work implementation status of the work stored in a memory based on the work target and work content of the work that are identified, and controls to display the work implementation status of the work based on the work implementation status information on a display terminal connected through a network.

BRIEF DESCRIPTION OF THE DRAWINGS

A more complete appreciation of the embodiments and many of the attendant advantages and features thereof can be readily obtained and understood from the following detailed description with reference to the accompanying drawings, wherein:

FIG. 2 is a block diagram illustrating a hardware configuration of a business server 10 according to the first embodiment of the present disclosure;

FIG. 5 is a diagram illustrating an example of a configuration of a staff information storage unit;

FIG. 6 is a diagram illustrating an example of a configuration of a voice text storage unit;

FIG. 7 is a diagram illustrating an example of an utterance pattern;

FIG. 8 is a diagram illustrating an example of updating a voice text storage unit;

FIG. 11 is a diagram illustrating an example of a configuration of a work implementation status storage unit;

FIG. 12 is a diagram illustrating a display example of a work implementation status screen;

FIG. 13 is a diagram illustrating an example of a configuration of a work master storage unit;

FIG. 14 is a diagram illustrating a display example of a message;

FIG. 18 is a diagram illustrating an example of a configuration of a work timing rule table.

Figure 1:
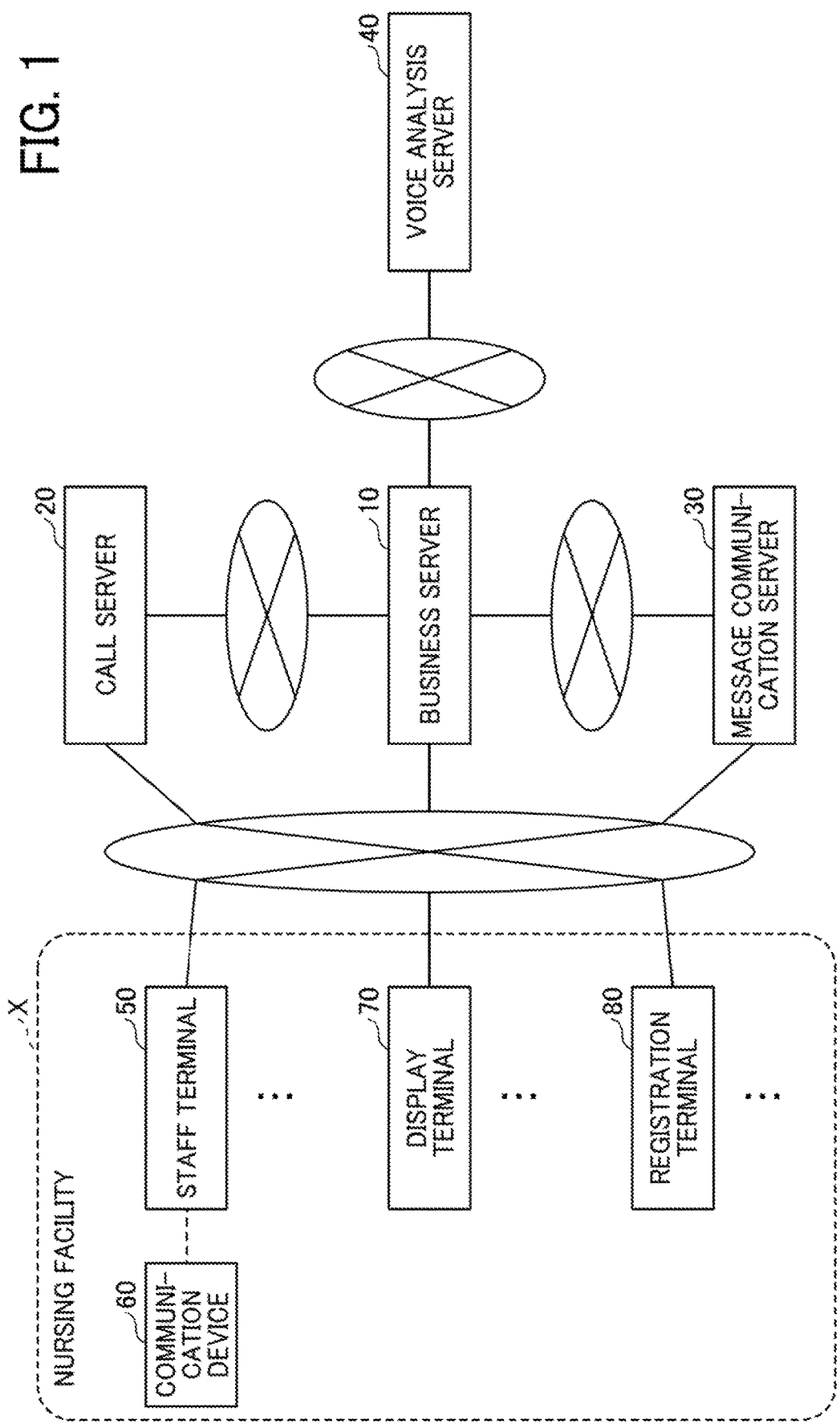
FIG. 1 is a block diagram illustrating a configuration of an information processing system according to a first embodiment of the present disclosure.

The accompanying drawings are intended to depict embodiments of the present disclosure and should not be interpreted to limit the scope thereof. The accompanying drawings are not to be considered as drawn to scale unless explicitly noted. Also, identical or similar reference numerals designate identical or similar components throughout the several views.

DETAILED DESCRIPTION

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result. As used herein, the singular forms "a", "an", and "the" are intended to include the plural forms as well, unless the context clearly indicates otherwise.

Embodiments of the present disclosure are described below with reference to the drawings. FIG. 1 is a block diagram illustrating a configuration of an information processing system according to a first embodiment of the present disclosure. In the present embodiment, nursing care work, which is work for residents (care recipients) in the nursing facility X performed by a plurality of care staff members (hereinafter simply referred to as "staff members") at a nursing facility X, is described as an example of the work performed by the worker, but the care work may be performed by one staff member for one or more residents (care recipients) in the nursing facility X.

In the nursing facility X illustrated in FIG. 1, each of a plurality of staff members carries one communication device 60 and one staff terminal 50. Further, in the nursing facility X, one or more display terminals 70 and one or more registration terminals 80 are installed at predetermined positions.

Each staff terminal 50, each display terminal 70, and each registration terminal 80 are connected to the business server 10 through a network such as the internet. Each staff terminal 50 is further connected to a call server 20 and a message communication server 30 through a network such as the internet. The business server 10 is connected to the call server 20, the message communication server 30, and the voice analysis server 40 through a network such as the internet.

The communication device 60 is an intercom or a transceiver and includes a microphone and an earphone. The communication device 60 may have a wearable shape like a headset or a shape that can be held in a hand and used. The staff terminal 50 is, for example, a smartphone or a tablet terminal. The staff terminal 50 can communicate with the communication device 60 by short-range wireless communication.

The staff terminal 50 receives voice data from the communication device 60, indicating voice (that is, content of utterance of the staff member) input by the communication device 60, transmits the voice data to the call server 20, and receives and outputs the voice data distributed from the call server 20. The staff terminal 50 also receives text data in which the voice data from each staff terminal 50 is converted into text and distributed from the message communication server 30 connected through the internet or the like and displays the text data. As a result, each staff member can know the contents of work performed by other staff members by voice and text.

The call server 20 is one or more computers that support voice call between the staff terminals 50. The call server 20 distributes the voice data transmitted from one of the staff terminals 50 to each of the other staff terminals 50.

The registration terminal 80 is a computer such as a personal computer (PC) that receives input of information indicating a work schedule for each resident (hereinafter referred to as "work schedule information") and registers the work schedule information in the business server 10. The work schedule information is information indicating order of performing work in time series.

The business server 10 is one or more computers that execute information processing specialized for work (care work) in the nursing facility X. For example, the business server 10 acquires voice data that the call server 20 receives from each staff terminal 50, and updates implementation status (progress status) of the work indicated by the work schedule information registered for each resident based on the voice data. That is, when carrying out the work, each staff member utters which staff member will work for which resident. The business server 10 grasps the implementation status of the work by using the voice data in which the content of the utterance is recorded.

The voice analysis server 40 is one or more computers that apply voice recognition to voice data received by the business server 10 from the staff terminal 50 and convert the voice data into text data. The business server 10 uses conversion result obtained by the voice analysis server 40 to update the work implementation status.

The message communication server 30 distributes the text data, which is the conversion result of the voice analysis server 40 for the voice data received by the business server 10, to each staff terminal 50. Therefore, each staff member can refer to the staff terminal 50 to check the history of the utterance content of each staff member.

The display terminal 70 is a PC, a tablet terminal, a smartphone, or the like that displays a comprehensive view of the implementation status of the work managed by the business server 10. As a result, all or some of the plurality of staff members can grasp current implementation status of the work for a plurality of residents.

FIG. 2 is a block diagram illustrating a hardware configuration of a business server 10 according to the first embodiment. The business server 10 in FIG. 2 includes a drive 100, an auxiliary storage device 102, a memory 103, a CPU 104, an interface 105, etc., which are connected to each other by a bus B.

A program that implements the processing in the business server 10 is provided by a storage medium 101 such as a compact disk-read only memory (CD-ROM). When the recording medium 101 storing the program is set in the drive 100, the program is installed in the auxiliary storage device 102 from the storage medium 101 through the drive 100. However, it is not always necessary to install the program from the storage medium 101 and the program may be downloaded from another computer through the network. The auxiliary storage device 102 stores the installed program and also stores necessary files and data.

The memory 103 reads the program from the auxiliary storage device 102 and stores the program when an instruction to activate the program is given. The CPU 104 executes a function related to the business server 10 according to a program stored in the memory 103. The interface 105 is used as an interface for connecting to a network.

The call server 20, the message communication server 30, the voice analysis server 40, the staff terminal 50, the display terminal 70, the registration terminal 80, and the like may also include hardware as illustrated in FIG. 2.

Figure 3A:
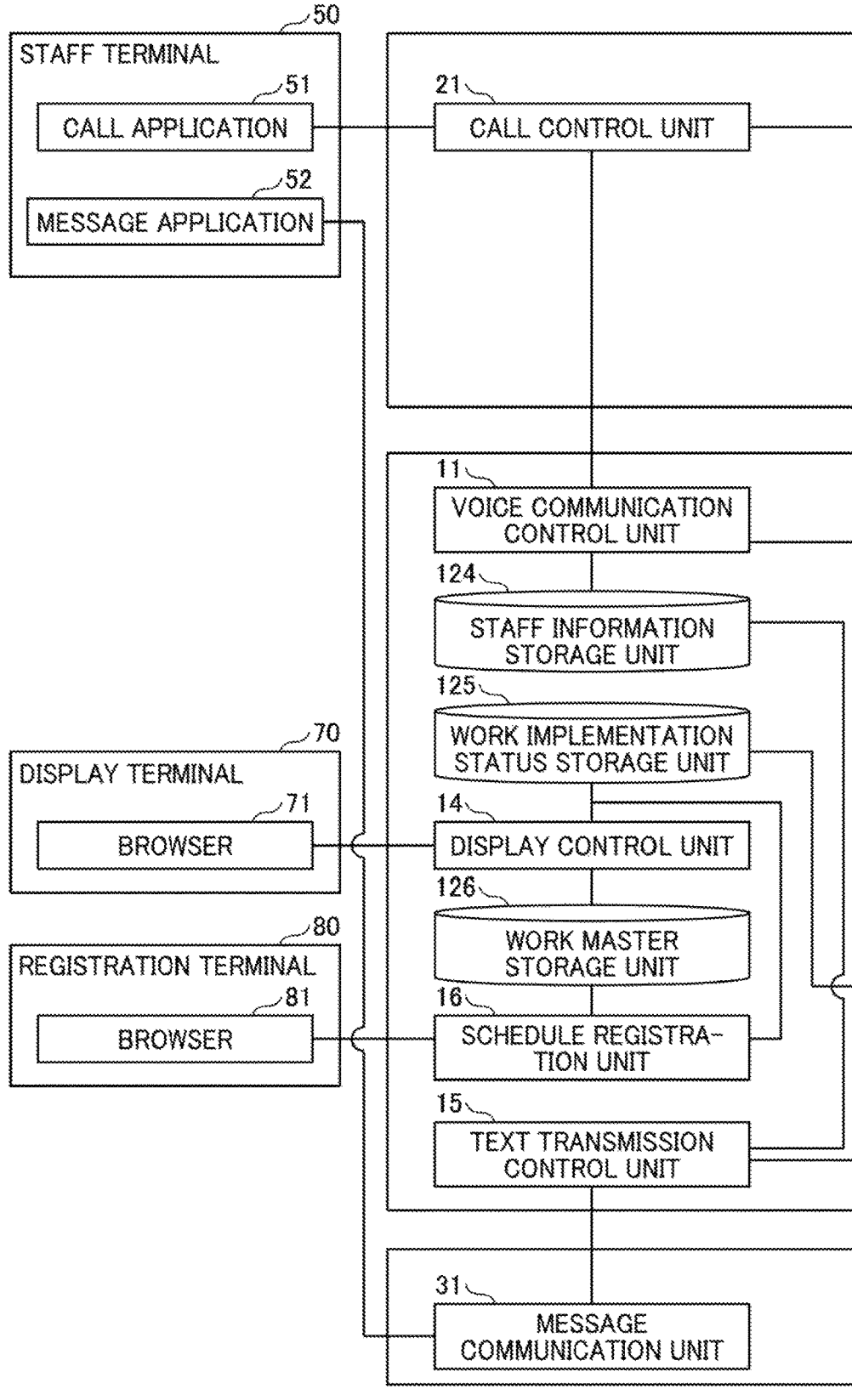
FIG. 3A and FIG. 3B are block diagrams illustrating a functional configuration of an information processing system according to a first embodiment of the present disclosure.
Figure 3B:
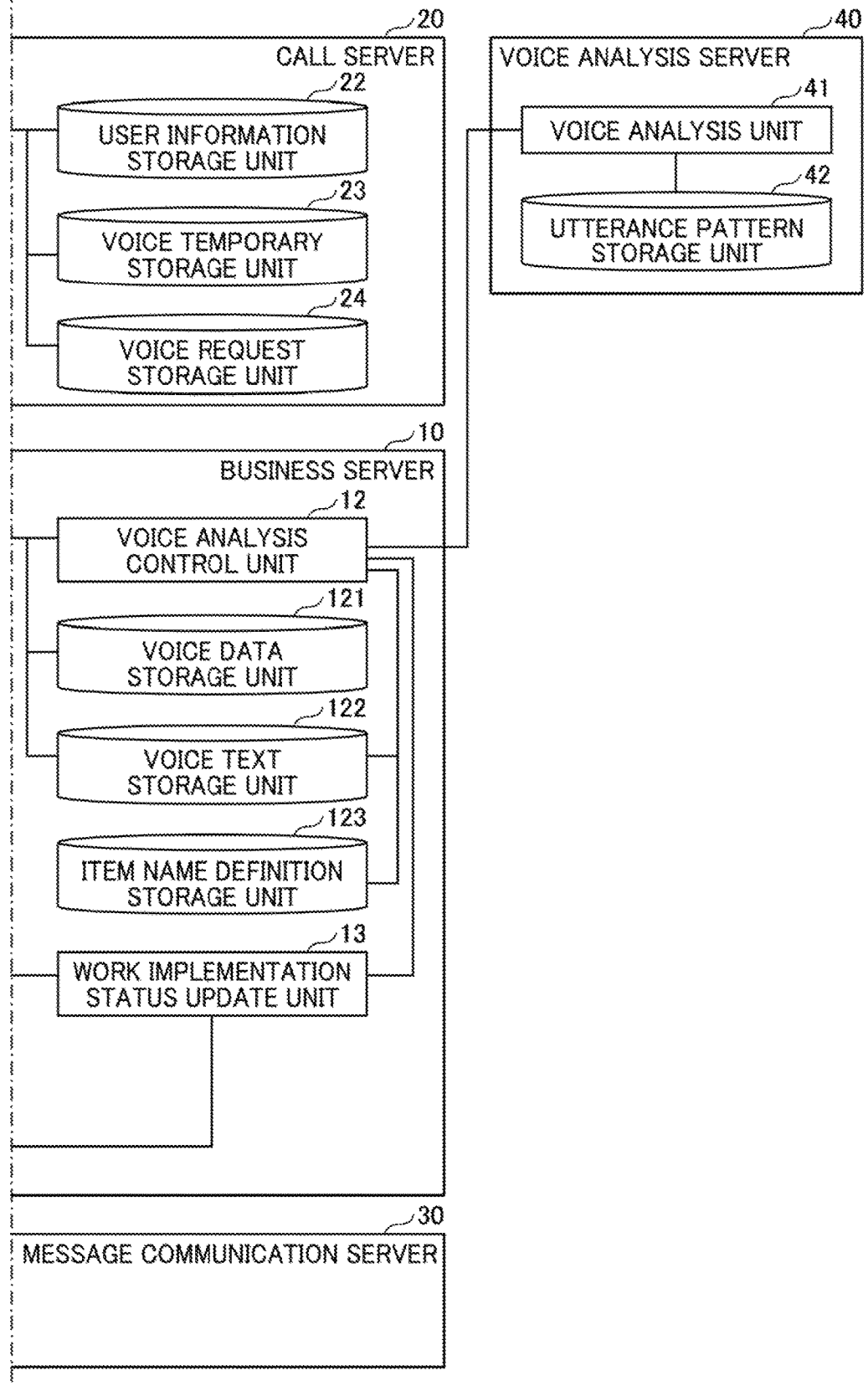

FIG. 3A and FIG. 3B are block diagrams illustrating a functional configuration of an information processing system according to the first embodiment. In FIG. 3A, the staff terminal 50 includes a call application 51, a message application 52, and the like. Each of these applications are implemented by a process executed by the staff terminal 50 caused by one or more programs installed on staff terminal 50. The call application 51 implements a call with another staff terminal 50 through the call server 20. The message application 52 is an application that receives a message transmitted from the message communication server 30 and displays the message.

The display terminal 70 includes a browser 71. The browser 71 is implemented by a process executed by the CPU of the display terminal 70 according to one or more programs installed on the display terminal 70. The browser 71 is a web browser that causes the display terminal 70 to display a screen indicating the implementation status of each work for each resident based on the display data acquired from the business server 10.

The registration terminal 80 includes a browser 81. The browser 81 is implemented by a process of causing the CPU of the registration terminal 80 to execute one or more programs installed in the registration terminal 80. The browser 81 is a web browser that causes the registration terminal 80 to display a screen for registering work schedule information for each resident and to transmit the schedule information input on the screen to the business server 10.

The call server 20 includes a call control unit 21. The call control unit 21 is implemented by a process executed by the CPU of the call server 20 according to one or more programs installed in the call server 20. The call server 20 also includes a user information storage unit 22, a voice temporary storage unit 23, a voice request storage unit 24, and the like. Each of these storage units is implemented by using, for example, an auxiliary storage device of the call server 20 or a storage device connectable to the call server 20 through a network.

The call control unit 21 controls a voice call (that is, voice data communication) between the call applications 51 of the staff terminals 50. The user information storage unit 22 stores information (user identifier (ID), etc.) regarding the user of the voice call service provided by the call server 20 (the user of the call application 51). The voice temporary storage unit 23 temporarily stores voice data received by the call control unit 21 from the staff terminal 50. The voice request storage unit 24 stores the user ID (staff ID described below) of the staff member who is requested to acquire the voice data from the business server 10.

The message communication server 30 includes a message communication unit 31. The message communication unit 31 is implemented by a process executed by the CPU of the message communication server 30 according to one or more programs installed in the message communication server 30. The message communication unit 31 transmits the message requested to be transmitted by the business server 10 to the message application 52 of the staff terminal 50.

The business server 10 includes a voice communication control unit 11, a voice analysis control unit 12, a work implementation status update unit 13, a display control unit 14, a text transmission control unit 15, a schedule registration unit 16, and the like. Each of these units is implemented by a process executed by the CPU 104 according to one or more programs installed in the business server 10. The business server 10 also includes a voice data storage unit 121, a voice text storage unit 122, an item name definition storage unit 123, a staff information storage unit 124, a work implementation status storage unit 125, a work master storage unit 126, and the like. Each of these storage units is implemented by using, for example, the auxiliary storage device 102 or a storage device that is connected to the business server 10 through a network.

The voice communication control unit 11 acquires, from the call server 20, voice data of each staff member whose staff ID is stored in the staff information storage unit 124 (that is, voice data in which the utterance content of each staff member is recorded). The staff ID is identification information of the staff member. The voice communication control unit 11 records the voice data in the voice data storage unit 121 and requests the voice analysis unit 41 to analyze the voice data. The staff information storage unit 124 stores a list of staff IDs.

The voice analysis control unit 12 requests the voice analysis server 40 to analyze the voice data requested to be analyzed by the voice communication control unit 11 and receives the analysis result by the voice analysis server 40. The analysis result includes text data indicating the utterance content recorded in the voice data and a keyword group included in the text data for identifying the work content. The voice analysis control unit 12 records the text data and the identification information (Uniform Resource Locator (URL)) of the storage destination (voice data storage unit 121) of the voice data in association with each other in the voice text storage unit 122. The voice analysis control unit 12 also identifies the meaning (item name) of each keyword based on the information stored in the item name definition storage unit 123 and notifies the work implementation information update unit of the identification result. The identification result is information indicating what kind of work was performed for which resident (that is, work content).

The work implementation status update unit 13 sends the information stored in the work implementation status storage unit 125, which indicates the implementation status of the work (work progress status) for each resident, based on the identified result communicated from the voice analysis control unit 12.

The display control unit 14 generates display data related to the screen based on the information stored in the work implementation status storage unit 125 and transmits the display data to the display terminal 70. The status of implementation of each work is displayed for each resident in the order of implementation of the work on the screen. When generating the display data, the display control unit 14 refers to the work master storage unit 126 to grasp the work implementation order and the like.

The schedule registration unit 16 registers the schedule information transmitted from the registration terminal 80 in the work implementation status storage unit 125. The work implementation status storage unit 125 stores the work schedule information for each resident and information indicating the implementation status of each work included in the schedule information.

The text transmission control unit 15 requests the message communication server 30 to transmit a message, which is text data, in response to the request from the work implementation status update unit 13.

The voice analysis server 40 includes a voice analysis unit 41. The voice analysis unit 41 is implemented by a process executed by the CPU of the voice analysis server 40 according to one or more programs installed in the voice analysis server 40. The voice analysis server 40 also includes an utterance pattern storage unit 42. The utterance pattern storage unit 42 is implemented by, for example, an auxiliary storage device of the voice analysis server 40, a storage device connected to the voice analysis server 40 through a network, or the like.

The voice analysis unit 41 applies voice recognition to the voice data requested to be analyzed by the voice analysis control unit 12 of the business server 10 and converts the voice data into text data. The voice analysis unit 41 also extracts a keyword from the text data based on the utterance pattern stored in the utterance pattern storage unit 42. The utterance pattern is information indicating the utterance pattern regarding the work performed by the staff member. In the present embodiment, a pattern of utterance content when performing each work is determined, and each staff member speaks based on the pattern. Since there are a plurality of types of utterance contents regarding work, a plurality of types of utterance patterns are stored in advance in the utterance pattern storage unit 42.

Note that the layout of the functional units illustrated in FIG. 3A and FIG. 3B is merely an example. For example, the business server 10 may serve as any one or more of the call server 20, the voice analysis server 40, and the message communication server 30, or other servers may be combined. The voice data may be stored in cloud storage service instead of the voice data storage unit 121.

Further, the call application 51 and the message application 52 included in the staff terminal 50 may be implemented by one application.

Figure 4A:
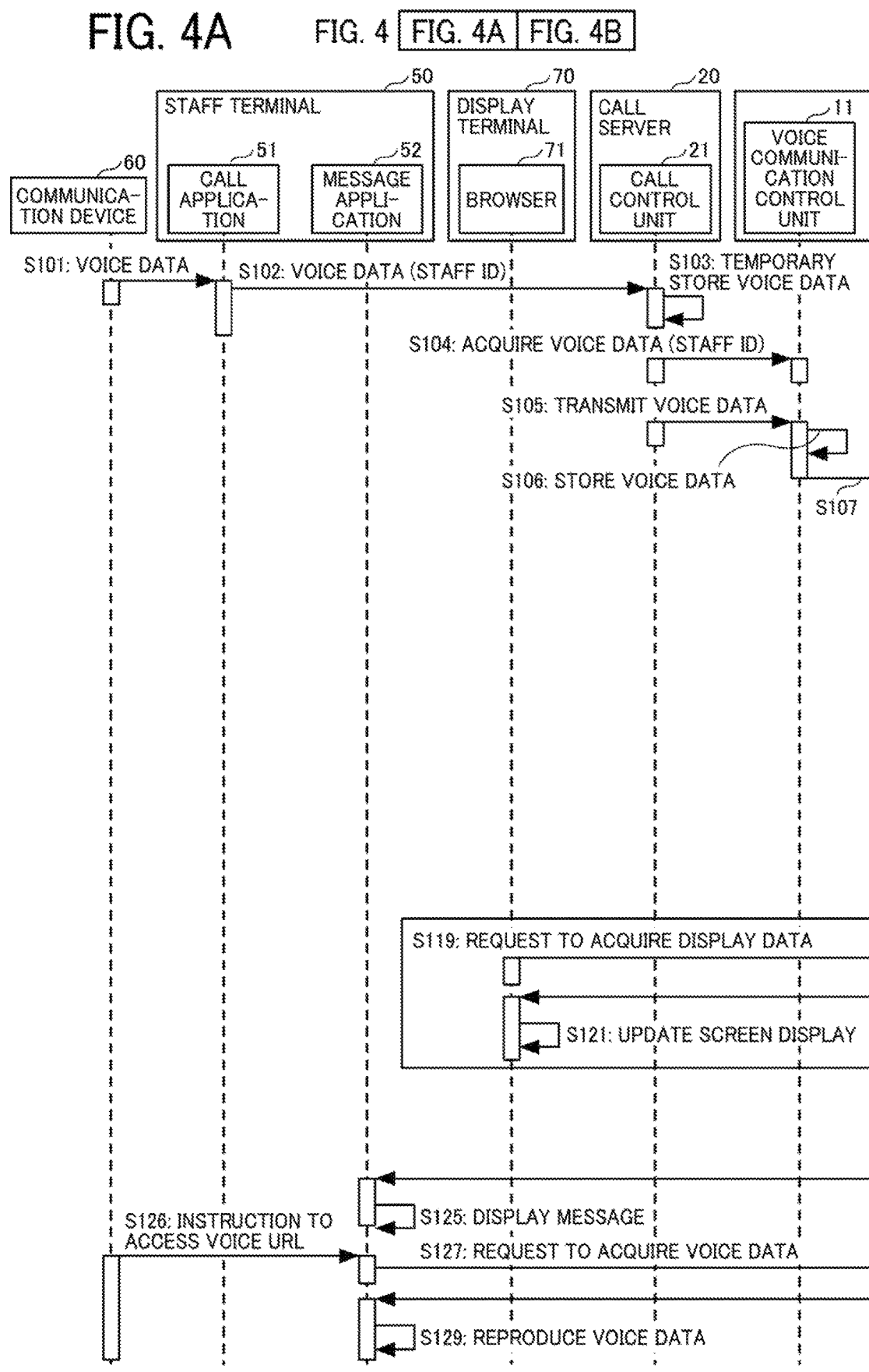
FIG. 4A and FIG. 4B are sequence diagrams illustrating an example of a process executed by the information processing system.
Figure 4B:
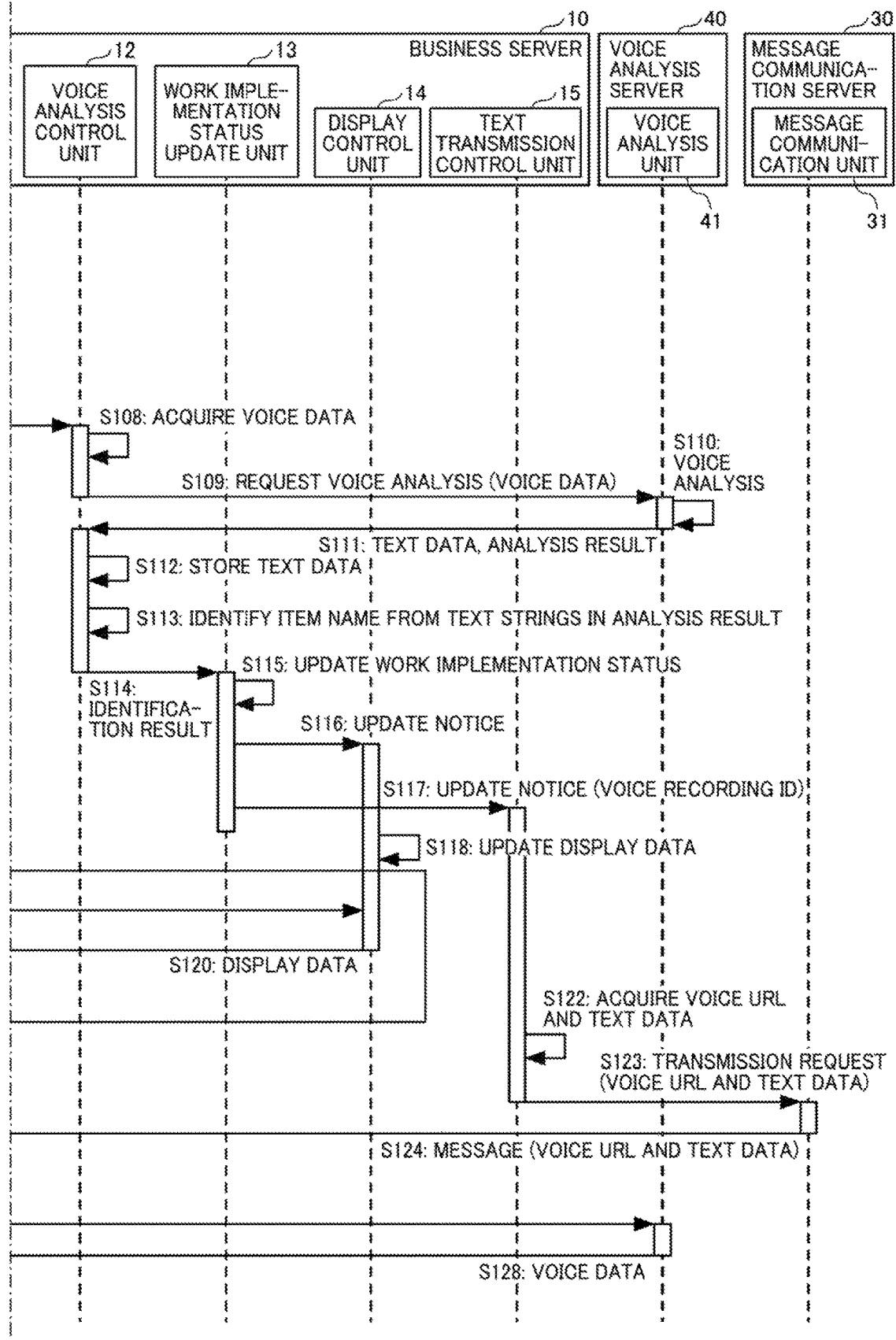

The process executed by the information processing system is described below. FIG. 4A and FIG. 4B are sequence diagrams illustrating an example of a process executed by the information processing system.

When one of the staff members (hereinafter referred to as "target staff member") makes an utterance related to the implementation of the work, the communication device 60 of the target staff member transmits the voice data (hereinafter referred to as "target voice data") indicating the content of the utterance to the staff terminal 50 of the staff member in step S101. In step S102, the call application 51 of the staff terminal 50 transmits the target voice data and the user ID of the call server 20 stored in advance in the staff terminal 50 to the call server 20. In the present embodiment, the staff ID is used as the user ID of the call server 20. The staff ID may be a common ID for a plurality of staff members. The staff ID may be an ID for a group of a plurality of staff members.

In step S103, in response to receiving the target voice data and the staff ID (hereinafter, referred to as "target staff ID"), the call control unit 21 of the call server 20 associates the target voice data with the target staff ID and temporarily stores the target voice data and the target staff ID in the voice temporary storage unit 23. Note that the call control unit 21 distributes the target voice data to the staff terminals 50 other than the staff terminal 50 that is the transmission source of the target voice data. The process relating to the distribution may follow a known technique. As a result, each staff member can hear the voice related to the target voice data.

In step S104, the voice communication control unit 11 of the business server 10 transmits a voice data acquisition request to the call control unit 21. A list of staff IDs stored in advance in the staff information storage unit 124 is designated for the voice data.

FIG. 5 is a diagram illustrating an example of a configuration of a staff information storage unit 124. As illustrated in FIG. 5, the staff information storage unit 124 stores the staff ID and a message user ID for each staff member in the nursing facility X. In step S104, a list of staff ID is referred to. On the other hand, the message user ID is a user ID of each staff member for the message exchange service provided by the message communication server 30.

The call control unit 21 records the staff ID designated in the acquisition request in the voice request storage unit 24. As a result, when the voice data associated with the staff ID included in the list is received by the call server 20, a session for establishing transfer of the voice data to the business server 10 is set up between the call control unit 21 and the voice communication control unit 11. Note that step S104 may be executed for each staff ID. In this case, a session is set up for each staff ID. Further, in FIG. 4A, step S104 is illustrated to be executed after step S103, but step S104 may be executed before step S103.

In step S105, the call control unit 21 transmits the target voice data to the voice communication control unit 11 of the business server 10 through the session corresponding to the target staff ID if any of the user IDs stored in the voice request storage unit 24 matches with the target staff ID associated with the target voice data stored in the voice temporary storage unit 23 in step S104.

In step S106, upon receiving the target voice data, the voice communication control unit 11 stores the target voice data in the voice data storage unit 121, and stores identification information such as URL or the like of the storage destination of the target voice data in the voice text storage unit 122.

FIG. 6 is a diagram illustrating an example of a configuration of a voice text storage unit 122. As illustrated in FIG. 6, the voice text storage unit 122 stores a voice record ID, staff ID, voice URL, and text data for each voice data.

The voice record ID is identification information of voice data and is assigned by the voice communication control unit 11 in step S106. The staff ID indicates the staff member of the utterance source of the voice data. When a session is set up for each staff ID, the staff ID is identified based on the session used to receive the voice data. On the other hand, when a common session is set up for a plurality of staff IDs, the staff ID may be transmitted from the call control unit 21 in addition to the voice data. In this case, the staff ID received together with the voice data is stored in the voice text storage unit 122 in association with the voice data. The voice URL indicates the storage destination of the voice data. The text data is obtained as a result of applying voice recognition to the voice data.

At the time of step S106, no text data has been obtained for the target voice data. Therefore, the voice communication control unit 11 generates a voice record ID (hereinafter, referred to as "target voice record ID") for the target voice data, and stores a record (hereinafter, referred to as "target record") that includes the target voice record ID, the target staff ID, and the voice URL but does not include text data in the voice text storage unit 122. For example, in FIG. 6, the record having the voice record ID "0004" is an example of the record stored in step S106.

In step S107, the voice communication control unit 11 notifies the voice analysis control unit 12 of the target voice record ID. In step S108, the voice analysis control unit 12 acquires voice data (target voice data) from the voice data storage unit 121 based on the target voice record ID. Specifically, the voice analysis control unit 12 acquires the voice data stored in the storage destination identified by the voice URL stored in the voice text storage unit 122 in association with the target voice record ID. In step S109, the voice analysis control unit 12 transmits an analysis request for the target voice data including the target voice data to the voice analysis server 40.

In step S110, in response to receiving the analysis request, the voice analysis unit 41 of the voice analysis server 40 executes the analysis process on the target voice data included in the analysis request. In the analysis process, conversion (voice recognition) of target voice data into text data (hereinafter referred to as "target text data") and extraction of a keyword group from the target text data are performed. The utterance pattern stored in the utterance pattern storage unit 42 is used to extract the keyword group.

FIG. 7 is a diagram illustrating an example of the utterance pattern. The utterance pattern p1 illustrated in FIG. 7 is an example of one utterance pattern in the utterance pattern group stored in the utterance pattern storage unit 42. In the utterance pattern p1, the character string enclosed in a parenthesis "( )" is a keyword (character string) indicating a work item or a work sub-item and is a default value in the utterance pattern. In the utterance pattern p1, "preprandial medication" in the first parenthesis "( )" indicates a work item, and "identity confirmation" in the second parenthesis "( )" indicates a work sub-item. The work item is the highest-level concept that classifies multiple types of work. The work sub item is a concept of subdividing the work item. Work items and work sub-items belonging to each work item are defined in advance as described below.

On the other hand, a value enclosed by a bracket "[ ]" is a variable. The first bracket "[ ]" in the utterance pattern p1 is a keyword that identifies a resident who is the target of the work, "preprandial medication" (hereinafter referred to as "resident ID"). The resident ID includes, for example, as illustrated in FIG. 7, a character string "room", a number indicating a room number, a title added to the name "Mr." or "Ms." and the name of the resident. The second bracket "[ ]" in the utterance pattern p1 is a keyword indicating the work result. The work result is represented by, for example, "completed", "OK", "done", etc., as illustrated in FIG. 7.

Each staff member is trained to speak in a format that matches the utterance pattern corresponding to the work performed by the staff member. For example, if the target text data, which is the result of voice recognition by the voice analysis unit 41, is "preprandial medication room 101 Mr. A identity confirmation OK", the voice analysis unit 41 extracts the utterance patterns that includes all parts (that is, work items and work sub-items) enclosed by the parenthesis "( )" in the target text data from the utterance pattern group stored in the utterance pattern storage unit 42. Therefore, in the case of "preprandial medication room 101 Mr. A identity confirmation OK", the utterance pattern p1 in FIG. 7 is extracted.

The voice analysis unit 41 extracts the resident ID and the work result from the target text data based on the extracted utterance pattern p1. The voice analysis unit 41 generates, as an analysis result, data in which each keyword is arranged in the order of work item, resident ID, work sub-item, and work result. Specifically, for "preprandial medication room 101 Mr. A identity confirmation OK", "preprandial medication, room 101 Mr. A, identity confirmation, work result" is generated as an analysis result based on the utterance pattern p1.

If the target text data does not include any work item and any work sub-item and the utterance pattern corresponding to the target text data cannot be identified, the voice analysis unit 41 generates, for example, an empty analysis result. Such text data is not based on utterances regarding work execution but based on utterances regarding other topics. Therefore, by generating an empty analysis result, erroneous execution of the process described below due to an utterance not related to the execution of the work is avoided.

In step S111, the voice analysis unit 41 transmits a response including the target text data and the analysis result (array of the extracted keywords) to the voice analysis control unit 12 of the business server 10.

In step S112, in response to receiving the response, the voice analysis control unit 12 stores the target text data included in the response in the target record of the voice text storage unit 122. As a result, the voice text storage unit 122 is updated as illustrated in FIG. 8.

FIG. 8 is a diagram illustrating an example of updating a voice text storage unit 122. In FIG. 8, the target text data is stored in the record with voice record ID "0004".

Steps S113 and thereafter are not executed when the analysis result included in the response from the voice analysis unit 41 is empty.

In step S113, the voice analysis control unit 12 identifies the item name for each keyword included in the analysis result in the response from the voice analysis unit 41 by referring to the item name definition storage unit 123. Identifying the item name is equivalent to identifying the meaning of each keyword.

Figures 9, 10:
FIG. 9 is a diagram illustrating an example of a configuration of an item name definition storage unit.
FIG. 10 is a diagram illustrating an example of an item name identification result.

FIG. 9 is a diagram illustrating an example of a configuration of the item name definition storage unit 123. As illustrated in FIG. 9, the item name definition storage unit 123 stores the item name in association with the order of the keywords in the analysis result. In the example of FIG. 9, the first keyword of the analysis result is "work item", the second keyword is "resident ID", the third keyword is "work sub-item", and the fourth keyword is "work result". For example, when the analysis result is "preprandial medication room 101 Mr. A identity confirmation OK", for each keyword included in the analysis result, the item name is identified as illustrated in FIG. 10.

FIG. 10 is a diagram illustrating an example of item name identification result. In an example illustrated in FIG. 10, "preprandial medication" is identified as the work item, "room 101 Mr. A" is identified as the resident ID, "identity confirmation" is identified as the work sub-item, and "OK" is identified as the work result.

In step S114, the voice analysis control unit 12 notifies the work implementation status update unit 13 of the identification result illustrated in FIG. 10. In step S115, the work implementation status update unit 13 updates the work implementation status in the work implementation status storage unit 125 if the value of the "work result" in the identified result is a predetermined value indicating success of the work, such as "completed", "OK", "completed", "done". On the other hand, if the value of the "work result" is a value indicating the failure of the work, steps S115 and S116 are not executed.

FIG. 11 is a diagram illustrating a configuration example of the work implementation status storage unit 125. As illustrated in FIG. 11, one record stored in the work implementation status storage unit 125 stores schedule information and work implementation status information for one work for one resident. Usually, multiple items of work are scheduled to be performed for one resident each day. Therefore, a plurality of records are registered in the order in which work is performed for each resident each day. For example, in the example of FIG. 11, a plurality of records having the resident ID of "room 101 Mr. A" are registered. These records are the work scheduled to be performed for "room 101 Mr. A" arranged in the order of implementation.

The value of each item included in the schedule information is registered in advance from the registration terminal 80. The schedule information includes items such as resident ID, date, work item and work sub item. The resident ID indicates the resident who is the target of the work to be performed. The date indicates the date on which the work is to be performed. The work item and the work sub-item indicate the work to be performed.

On the other hand, the value of each item included in the work implementation status information is registered based on the voice data regarding the implementation of the work. The work implementation status information includes items such as the work result, the staff ID, and the voice record ID. The work result is an item indicating the result of performing the work. The staff ID indicates the staff member who performed the work. The voice record ID indicates voice data of a voice uttered when performing the work.

In step S115, the work implementation status update unit 13 identifies a record to be updated from the records of the work implementation status storage unit 125 based on the identification result as illustrated in FIG. 10. Specifically, the record including the work item, the resident ID, and the work sub-item of the specific result and the schedule information in which the value of "date" is the current day (hereinafter referred to as "update target record") is identified as the record to update. The work implementation status update unit 13 records the current time (that is, the time at which the work is performed), the target staff ID, and the target for each of the "work result", "staff ID"; and "voice record ID". As a result, the work implementation status (actual results) regarding the work associated with the update target record is stored in the work implementation status storage unit 125.

If a value is already stored in each item of the work implementation status information of the record identified as the update target record, the same work has been redone. In this case, the work implementation status update unit 13 creates a copy of the update target record immediately below the update target record and updates the work implementation status information of the copied record as described above. As a result, the fact that the same work has been redone is recorded as a history.

In steps S116 and S117, the work implementation status update unit 13 transmits a notification of the update of the work implementation status information to each of the display control unit 14 and the text transmission control unit 15 respectively. At this time, the notification to the text transmission control unit 15 includes the target voice record ID.

In step S118, in response to the update notification from the work implementation status update unit 13, the display control unit 14 refers to the updated work implementation status storage unit 125 to generate or update the display data of the work implementation status screen. The display data includes, for example, HyperText Markup Language (HTML) and script.

In response to the display data acquisition request transmitted from the browser 71 of the display terminal 70 in step S119, the display control unit 14 causes the display terminal 70 to display the display data by transmitting a response including the display data generated in step S118 to the browser 71 in step S120. In step S121, when the browser 71 receives the display data, the browser 71 updates the work implementation status screen based on the display data.

The browser 71 accesses the display control unit 14 identified by the URL of the work implementation status screen in accordance with an operation of any staff member on the display terminal 70, and displays the work implementation status screen based on the display data generated according to the work implementation status storage unit 125 at that time. After that, the browser 71 transmits a display data acquisition request to the display control unit 14 at a fixed time intervals (for example, every one second) based on the definition of the script included in the display data. As a result, the browser 71 displays a work implementation status screen corresponding to the most recent status of the work implementation status storage unit 125.

FIG. 12 is a diagram illustrating a display example of the work implementation status screen. In the work implementation status screen 510 illustrated in FIG. 12, work implementation status of a resident is displayed in a row, and work items and work sub items are displayed in a respective column.

Residents are identified by room number and name. In each row, the time of the work performed and the staff ID of the staff member who performed the work are displayed in the column of the work item (work sub-item) performed on the resident in the row. These values can be obtained by referring to the work implementation status storage unit 125.

The arrangement order of the work items and work sub-items in the column direction is based on the information stored in the work master storage unit 126.

FIG. 13 is a diagram illustrating an example of a configuration of the work master storage unit 126. As illustrated in FIG. 13, the work master storage unit 126 stores work items and work sub-items belonging to each work item in association with each other. The work master storage unit 126 basically stores each work item in the order of execution within one day and stores each work sub-item in the order of execution within each work item. When generating display data, the display control unit 14 assigns work items and work sub-items to each column of the work implementation status screen 510 in the order defined in the work master storage unit 126.

The work master storage unit 126 is also used when the schedule registration unit 16 creates a registration screen displayed on the registration terminal 80 when the schedule is registered in the work implementation status storage unit 125. (That is, when a new record is generated in the work implementation status storage unit 125 and the value of each item of the schedule information of the record is recorded.)

Note that the work implementation status screen 510 of FIG. 12 includes a column "absent" in addition to the work items. The column indicates whether or not the resident is present in the nursing facility X on that day, and a check is set in the column for a resident who is absent (for example, when a resident is temporarily returning home). Whether or not the resident is absent on the day is determined by the display control unit 14 referring to the work implementation status storage unit 125. That is, the display control unit 14 determines that a resident for whom no record including the "date" corresponding to the current day is registered is absent.

Further, for example, in the row of Mr. B in room 102, the column of preprandial medication is shaded. This is based on the schedule information for the work item of the resident not registered in the work implementation status storage unit 125. That is, the display control unit 14 generates the work implementation status screen 510 so that the column of work item for which schedule information is not registered is shaded. In addition, a mode other than shading may be used to indicate that the work item or the work sub-item is not scheduled.

For example, all staff members or some staff members such as leaders can obtain a comprehensive view of the work implementation status of each resident by referring to the work implementation status screen 510 as illustrated in FIG. 12. Therefore, it is possible to efficiently grasp the omission of the work performed for any of the residents. Specifically, it is possible to reduce the need for each staff member to confirm with another staff member that a particular work has been performed by a particular staff member.

Returning to FIG. 4, in step S122, the text transmission control unit 15 that has received the update notification in step S117 acquires the voice URL and the text data associated with the voice record ID included in the notification from the voice text storage unit 122 illustrated in FIG. 8. In step S123, the text transmission control unit 15 transmits a message transmission request including the voice URL and the text data to the message communication server 30. In the transmission request, a list of message user IDs stored in the staff information storage unit 124 is designated as identification information of the message transmission destination.

In step S124, upon receiving the transmission request, the message communication unit 31 of the message communication server 30 transmits the message related to the transmission request to each message user ID designated in the transmission request. As a result, the message is transmitted to the message application 52 of each staff terminal 50.

In step S125, upon receiving the message, the message application 52 of each staff terminal 50 causes the staff terminal 50 to display the message.

FIG. 14 is a diagram illustrating a display example of a message. As illustrated in FIG. 14, on the screen displayed by the message application 52 on the staff terminal 50, the history of messages received from the message communication server 30 is arranged in the order of reception. Each message includes the text data and the voice URL included in the message. Here, the text data is the utterance content of the staff member regarding the work performed by the staff member. Therefore, each staff member can confirm the history of the work so far by referring to the screen.

The voice URL is included in the message as a link. In step S126, when any staff member inputs an instruction to access the voice URL (link) of any message, the message application 52 transmits a voice data acquisition request for the voice URL to the text transmission control unit 15 in step S127. Upon receiving the acquisition request, the text transmission control unit 15 acquires the voice data related to the voice URL from the voice data storage unit 121 and transmits a response including the voice data to the message application 52 in step S128. Upon receiving the response, the message application 52 causes the staff terminal 50 to reproduce the voice data included in the response in step S129. Consequently, each staff member can confirm the contents of past utterances by voice.

Note that, for example, the display control unit 14 may link the value in the column of work sub-item in each row of the work implementation status screen 510 illustrated in FIG. 12 to the voice URL corresponding to the value. In this case, when any of the links is selected on the work implementation status screen 510, the browser 71 of the display terminal 70 transmits a request for acquiring voice data associated with the voice URL corresponding to the link to the display control unit 14. The display control unit 14 acquires the voice data related to the voice URL from the voice data storage unit 121 and transmits a response including the voice data to the browser 71. The browser 71 causes the display terminal 70 to reproduce the voice data. Consequently, the staff member who browses the work implementation status screen 510 can confirm the utterance content regarding each work by voice through the work implementation status screen 510.

As described above, according to the first embodiment, based on the voice data transmitted from the terminal for inputting the utterance related to the work by the staff member, the work target and work content of the work are identified, the work implementation status information stored in the work implementation status storage unit 125 is stored based on the work target and the work content of the identified work, and the work implementation status based on the work implementation status information is displayed on the display terminal 70. Therefore, it is possible to support the grasp of the work implementation status of the work target.

Also according to the first embodiment, the work implementation status information stored in the work implementation status storage unit 125 is sequentially updated based on the voice data indicating the utterance content by each staff member, and a screen displaying the work implementation status information is displayed on the display terminal 70. Therefore, a staff member can grasp the implementation status (progress status) of the work for each resident on a comprehensive view. As a result, it is possible to assist in grasping the implementation status of work performed by a plurality of staff members.

Hereinafter, a description is given of a second embodiment. In the second embodiment, points different from the first embodiment is described. Points that are not particularly mentioned may be the same as described in the first embodiment.

Figure 15:
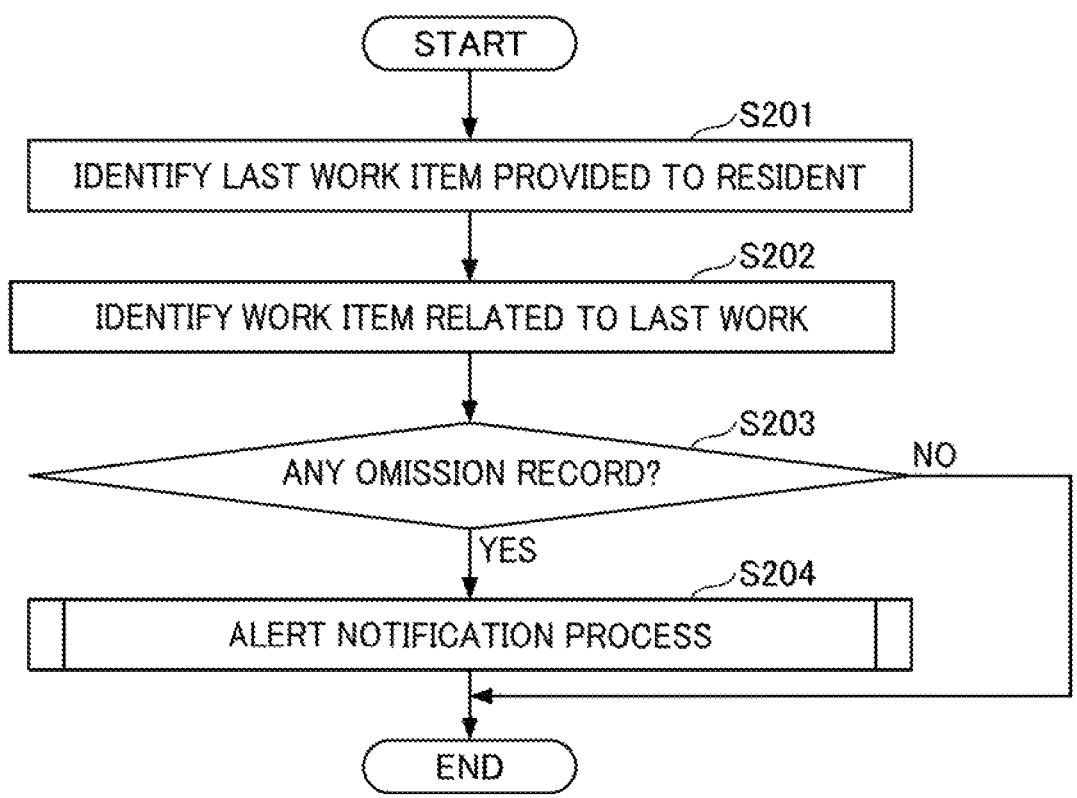
FIG. 15 is a flowchart illustrating an example of a process executed by the work implementation status update unit in a second embodiment of the present disclosure.

In the second embodiment, the work implementation status update unit 13 determines whether or not the work performed by the staff member satisfies a predetermined condition by executing the process illustrated in FIG. 15 before executing the step S115 illustrated in FIG. 4.

FIG. 15 is a flowchart illustrating an example of a process executed by the work implementation status update unit 13 in the second embodiment.

In step S201, the work implementation status update unit 13 identifies the last work item recorded in the work implementation status storage unit 125 illustrated in FIG. 11 regarding the resident (hereinafter referred to as a "target resident") associated with the resident ID (hereinafter referred to as a "target resident ID") included in the identification result illustrated in FIG. 10, notified in step S114. Specifically, the work implementation status update unit 13 selects the last record of the records including the target resident ID in the work implementation status storage unit 125 (hereinafter referred to as a "final work record"), in which a value is recorded in each item of the work implementation status information.

In step S202, the work implementation status update unit 13 identifies, in the work implementation status storage unit 125, a record (hereinafter, referred to as a "target work record") corresponding to the identification result illustrated in FIG. 10, notified in step S114. That is, in the work implementation status storage unit 125, a record including the target resident ID, the work item and the work sub-item included in the identification result is identified as the target work record.

In step S203, the work implementation status update unit 13 determines whether or not there is work that is not implemented. Specifically, the work implementation status update unit 13 determines whether or not there is a record between the final work record and the target record. That is, the work implementation status storage unit 125 stores records in the work implementation order. Therefore, when there is a record between the final work record and the target work record, the work related to the record (hereinafter; referred to as an "omission record") is not completed. In addition, in order to perform such determination more strictly, whether or not there is a record including the target resident ID, in which the work implementation status information is not recorded, between the final work record and the target record may be determined. As described above, in the second embodiment, whether the work item indicated by the target voice data satisfies a scheduled work execution order is determined.

When there is no omission record (No in step S203), step S115 and the subsequent steps are executed as described in the first embodiment. If there is an omission record (Yes in step S203), alert notification process is executed in step S204. When the alert notification process is executed, steps S115 and S116 in FIG. 4 are not executed.

Figure 16:
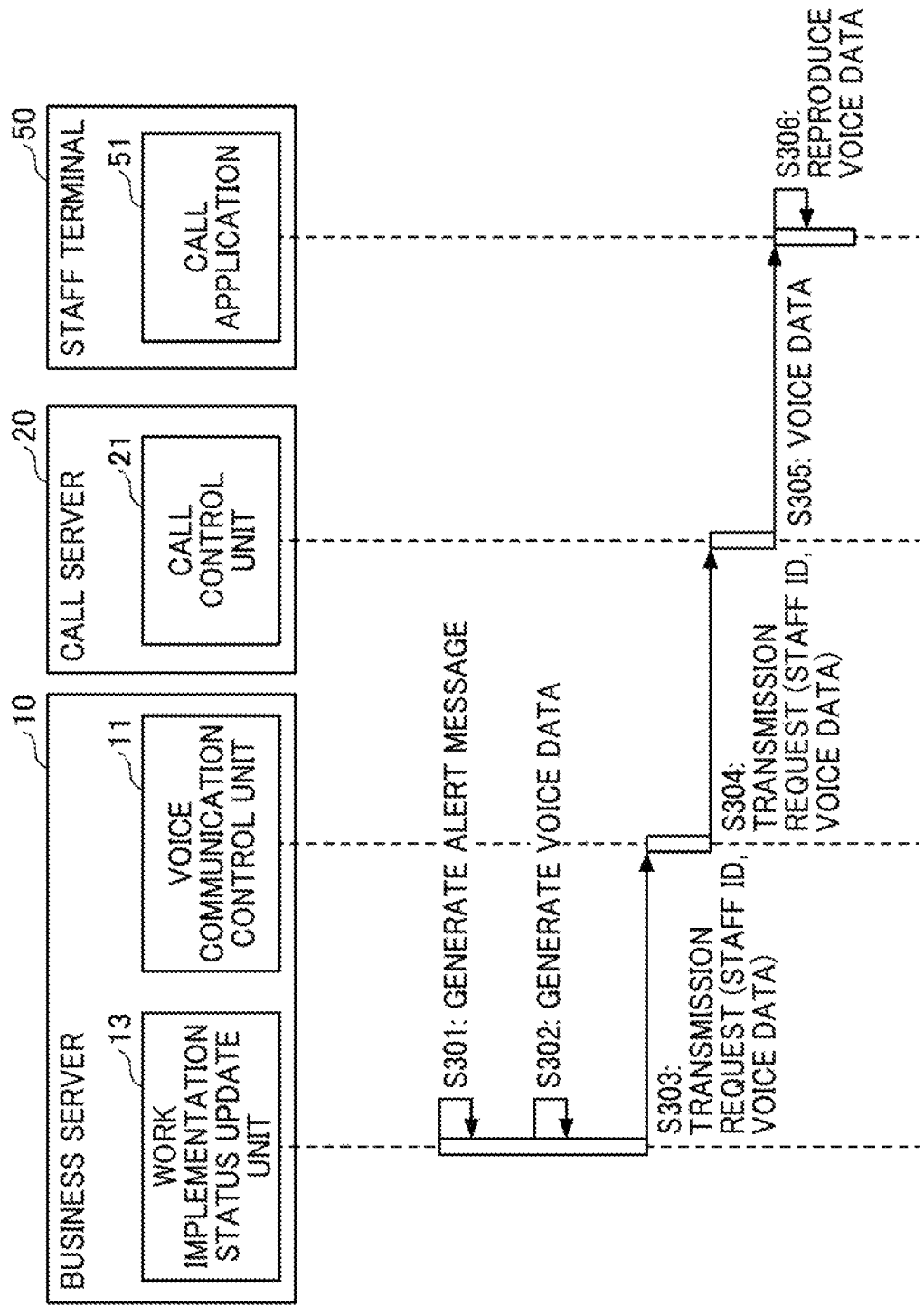
FIG. 16 is a sequence diagram illustrating an example of a process of alert notification.

Hereinafter, details of step S204 is described. FIG. 16 is a sequence diagram illustrating an example of the alert notification process.

In step S301, the work implementation status update unit 13 generates a character string (text data) indicating an alert message. The alert message is a message for warning the target staff member that there is an omission of work. The alert message is generated, for example, based on a template stored in advance in the auxiliary storage device 102.

Separate templates may be prepared for a case when the implementation of all of one work item (that is, all work sub-items belonging to the work item) is omitted (hereinafter, referred to as "case 1"), and a case when the implementation of one work sub-item is omitted (hereinafter referred to as "case 2").

In case 1, for example, the following template is used. "Please perform <omission work item> <omission work sub item>before <resident ID> <target work item>." In this case, the work implementation status update unit 13 applies the resident ID (target resident ID) of the omission record to <resident ID>, the work item of the target work record is applied to <target work item>, and the work item of the omission record is applied to <omission work record>. In case 1, there may be a plurality of omission records, but if the work items of all omission records are common, the work item is assigned to the <omission work item>. If the work items in the group are different (that is, if the implementation of two or more work items is omitted), the work item of the omission record that is the first in the implementation order in the omission record is applied to <omission work item>.

For example, when the target text data (text data related to the utterance) is "meal room 101 Mr. A starts", the work item (target work item) of the identified result notified in step S114 is "meal", and the work sub-item (target work sub-item) is "start". In this case, if the work item in the omission record is "preprandial medication", an alert message such as "please start preprandial medication before meal for room 101 Mr. A" is generated.

For example, in case 2, the following template is used. "Before <target work item> <target work sub-item> <resident ID>, please perform <work omission work item> <work omission work sub item>." In case 2, <target work sub-item> and <omission work sub-item> are added. In this case, the work implementation status update unit 13 further applies the work sub item of the target work record to <target work sub item> and the work sub item of the omission record to <omission work sub item>.

For example, the target text data (text data related to the utterance) is "preprandial medication room 101 Mr. A confirm swallowing", the work item (target work item) of the identified result notified in step S114 is "preprandial medication", and the work sub-item (target work sub-item) is "swallow confirmation". In this case, if the work item and work sub-item of the omission record are "preprandial medication" and "confirm medicine", an alert message such as "please check the preprandial medicine before preprandial medication swallow confirmation for room 101 Mr. A." is generated.

In step S302, the work implementation status update unit 13 generates voice data of the alert message (hereinafter referred to as "alert voice data"). A cloud service or the like that generates voice data from text data may be used to generate the alert voice data.

In step S303, the work implementation status update unit 13 requests the voice communication control unit 11 to transmit the alert voice data by designating the target staff ID as the destination. In step S304, the voice communication control unit 11 requests the call control unit 12 of the call server 20 to transmit the alert voice data by designating the target staff ID as the destination. In step S305, in response to the transmission request, the call control unit 21 transmits the alert voice data included in the transmission request to the call application 51 of the staff terminal 50 corresponding to the target staff ID designated in the transmission request. In step S306, in response to receiving the alert voice data, the call application 51 causes the staff terminal 50 of the target staff member to reproduce the alert voice data. As a result, the target staff member is notified of the omission work, and the work item or the work item and the work sub-item to be performed for the target resident.

Note that data in other formats such as character strings and image data may be used in addition to the voice data as the alert. In this case, the staff terminal 50 may display these data. Therefore, the voice communication control unit 11 may be configured as a communication control unit.

As described above, according to the second embodiment, whether the work identified based on the voice data indicating the utterance content by the staff member satisfies a predetermined condition (condition of the work implementation order) is determined, and if the condition is not met, an alert is sent to the staff member. Therefore, the staff member can know that his/her work does not satisfy the predetermined condition based on the alert and can avoid performing the wrong work. As a result, it is possible to prevent mistakes related to the work for the resident.

Hereinafter, a description is given of a third embodiment. In the third embodiment, points different from each of the above embodiments are described. The points that are not particularly mentioned may be the same as in the above-described embodiments.

Figure 17:
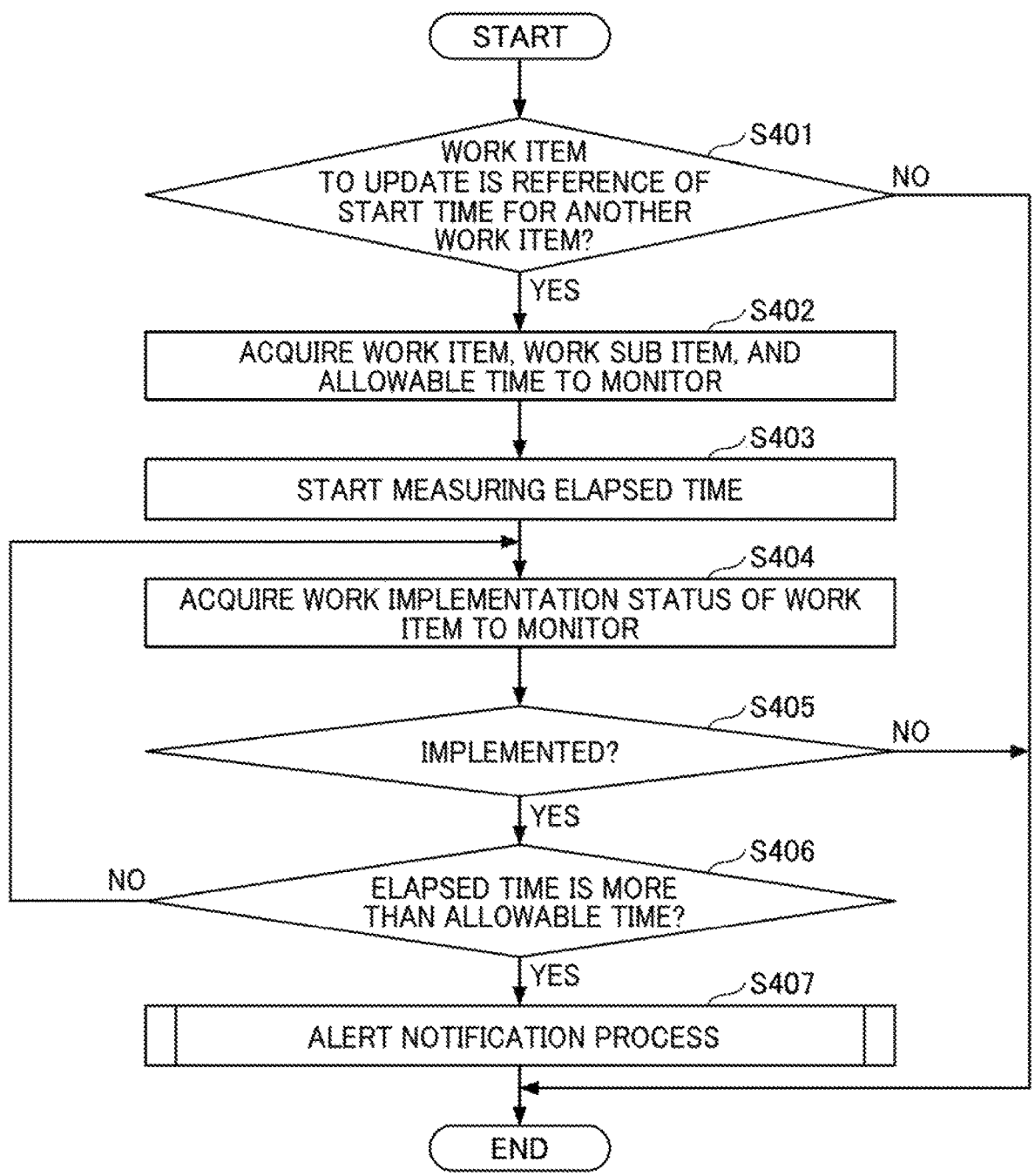
FIG. 17 is a flowchart illustrating an example of a process executed by the work implementation status update unit in a third embodiment of the present disclosure.

In the third embodiment, the work implementation status update unit 13 determines whether or not the work is satisfying a predetermined condition by executing the process illustrated in FIG. 17 after the execution of step S115 of FIG. 4. Note that the process of FIG. 17 may be executed in parallel with step S116 and subsequent steps of FIG. 4.

FIG. 17 is a flowchart illustrating an example of a process executed by the work implementation status update unit 13 in the third embodiment.

In step S401, the work implementation status update unit 13 determines whether the work item and the work sub-item related to the update target record in step S115 of FIG. 4 are references of start time of another work (hereinafter, referred to as "monitoring target work"). Such a determination is made, for example, by referring to a work timing rule table stored in advance in the auxiliary storage device 102.

FIG. 18 is a diagram illustrating an example of a configuration of a work timing rule table. As illustrated in FIG. 18, a record is registered in advance in the work timing rule table Ti for each candidate of the work to monitor the start time (hereinafter, referred to as "monitoring target work"). Each record includes a value of each item such as a work item to monitor, a work sub item to monitor, a reference work item, a reference work sub item, and an allowable time.

The work item to monitor indicates a candidate for the work item to monitor. The work sub-item to monitor indicates a candidate for the work sub-item to monitor. The reference work item indicates a work item of a work (hereinafter, referred to as "reference work") which is a reference of the start time of the candidate. The reference work sub-item is a work sub-item of the reference work. The allowable time is an allowable time with respect to the elapsed time from when the reference work is performed until when the candidate is executed. Note that, as illustrated in FIG. 18, the work sub item to monitor may be omitted. The first record in FIG. 18 indicates a rule that the postprandial medication must be administered within 30 minutes after the meal is completed.

In step S401, whether or not a record including the work item and the work sub-item relating to the update target record as the reference work item and the reference work sub-item is registered in the work timing rule table is determined.

In addition, if work interval is different for each resident, the work timing rule table may be defined for each resident. Alternatively, when a few of the residents (for example, one) has a different work interval from other residents, the work timing rule table for the few resident may be separately defined. A work timing rule table may be defined for each medicine to be taken.

If the corresponding record is not registered (No in step S401), the process after step S402 is not executed. When the corresponding record (hereinafter, referred to as "target record") is registered (Yes in step S401), the work implementation status update unit 13 acquires the monitoring target work item and the monitoring target work sub-item of the target record in step S402.

In step S403, the work implementation status update unit 13 starts measuring the elapsed time from the present time. For example, a timer may be activated.

In step S404, the work implementation status update unit 13 acquires the work implementation status information of the record including the target resident ID, the monitoring target work item, and the monitoring target work sub-item in the schedule information in the work implementation status storage unit 125 illustrated in FIG. 11. However, when the monitoring target work sub item is empty, the monitoring target work sub item corresponds to the first work sub item in the monitoring target work item.

In step S405, the work implementation status update unit 13 determines whether or not the monitoring target work item and the monitoring target work sub-item have not been implemented based on the work implementation status information. That is, if a value is not recorded in each item included in the work implementation status information, the monitored work item and the monitored work sub-item have not been implemented, and if the value is recorded, the monitored work item and the monitored work sub-item have already been implemented.

When the work item to monitor and the work sub item to monitor have been implemented (No in step S405), the work implementation status update unit 13 ends the process of FIG. 17. When the work item to monitor and the work sub item to monitor are not implemented (Yes in step S405), the work implementation status update unit 13 determines whether the elapsed time is equal to or longer than the allowable time of the target record in step S406. When the elapsed time is less than the allowable time of the target record (No in step S406), step S404 and subsequent steps are repeated. In this case, waiting for a predetermined time may be performed before executing step S404.

On the other hand, when the elapsed time is equal to or longer than the allowable time of the target record (No in step S406), the alert notification process is executed in step S407. As described above, in the third embodiment, whether or not the work implementation status satisfies the predetermined work implementation order condition is determined based on the target voice data.

Note that FIG. 17 illustrates an example in which the allowable time is set as a temporal condition for the elapsed time from a reference work, but for example, the time may be set as a temporal condition for some works. In this case, the work implementation status update unit 13 may execute the alert notification process when the work is not performed even at the time set for the work.

The alert notification process executed in step S407 is basically the same as the process illustrated in FIG. 16. However, the template used when generating the alert message in step S301 of FIG. 16 is different from the template in the second embodiment.

Specifically, in the third embodiment, for example, the following templates stored in the auxiliary storage device 102 in advance are used. "<allowable time> has passed since <reference work item> is completed. Please start <work item to monitor> of <resident ID>." For example, when the target record is the first row in FIG. 18, the work implementation status update unit 13 transmits the following alert message in step S301. "30 minutes have passed since the meal is completed. Please start postprandial medication for room 101 Mr. A".

Note that the destination of the alert message does not have to be limited to the target staff member because the alert message in the third embodiment is sent when the allowable time has passed since the target staff member performed work on the target resident. For example, in step S303 of FIG. 16, the work implementation status update unit 13 may request to transmit the alert voice data to the voice communication control unit 11 designating all staff IDs stored in the staff information storage unit 124 (FIG. 5) as transmission destinations. As a result, the alert voice data is reproduced on the staff terminals 50 of all staff members.

As described above, according to the third embodiment, whether the work identified based on the voice data indicating the utterance content by the staff member satisfies a predetermined condition (temporal condition) is determined, and if the condition is not met, an alert is sent to the staff member. The staff member can know that his/her work does not satisfy the predetermined condition based on the alert and can avoid omission of the work. As a result, it is possible to prevent mistakes related to the work for the resident.

In addition, in each of the above-described embodiments, the work in the nursing facility has been described as an example, but the above-described embodiments may be applied to other work performed by one or more workers on one or more work targets, such as work on a patient (work target) by a nurse (worker) in a hospital, construction work (work target) by construction workers (workers) at the construction site, car maintenance (work target) by a mechanic (worker) in a car maintenance shop, office work (work target) by staff (workers) in the office, and the like.

Note that the device group described in each of the above embodiments is merely one of a plurality of computing environments for implementing the embodiments described in the present disclosure.

In some embodiments, business server 10 includes multiple computing devices, such as a server cluster. The plurality of computing devices are configured to communicate with one another through any type of communication link, including a network, shared memory, etc., and perform the processes disclosed herein. Similarly, other servers may include multiple computing devices configured to communicate with one another.

Each function of the embodiments described above can be implemented by one or a plurality of processing circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

In the above embodiments, the business server 10 is an example of an information processing apparatus.

The above-described embodiments are illustrative and do not limit the present disclosure. Thus, numerous additional modifications and variations are possible in light of the above teachings. For example, elements and/or features of different illustrative embodiments may be combined with each other and/or substituted for each other within the scope of the present disclosure. Any one of the above-described operations may be performed in various other ways, for example, in an order different from the one described above.

What is claimed is:

1. An information processing apparatus comprising:
   circuitry configured to:
      register a schedule of work;

identify a work target and work content of the work, based on voice data sent from a terminal for inputting utterance about the work by a worker;
update work implementation status information indicating work implementation status of the work stored in a memory based on the work target and work content of the work that are identified and the schedule corresponding to the work target;
measure an elapsed time of the work target and work content of the work that are identified; and
control to display the work implementation status of the work based on the work implementation status information on a display terminal connected through a network, wherein
in a case where the elapsed time of the work target and work content of the work that are identified exceeds a threshold allowable time, the circuitry transmits an alert indicating that the work target and work content of the work that are identified remains incomplete is transmitted to the terminal.

2. The information processing apparatus of claim 1, wherein the circuitry is configured to
update, of work implementation status information corresponding to a plurality of work targets, the work implementation status information corresponding to the work target of the work that is identified.

3. The information processing apparatus of claim 2, wherein the work implementation status information is information indicating whether the work has been performed for each of the plurality of work targets, and the circuitry is further configured to
control to display on the display terminal whether the work has been performed for each of the plurality of work targets based on the work implementation status information.

4. The information processing apparatus of claim 1, wherein the circuitry is configured to
identify the work target and work content of the work based on analysis result of the voice data and definition info nation that defines correspondence between the work target, the work content, and the analysis result.

5. The information processing apparatus of claim 4, wherein the circuitry is further configured to:
convert the voice data into text data including a plurality of keywords;
identify a keyword for each of the work target and work content of the work, based on the plurality of keywords and definition information that defines correspondence between each of the work target and work content and each of the plurality of keywords; and
update the work implementation status information based on the keyword corresponding to the work target and work content of the work that are identified.

6. The information processing apparatus of claim 4, wherein the circuitry is further configured to:
transmit the text data converted from the voice data as analysis result of the voice data to the terminal;
identify the work target and work content of the work based on the analysis result of the voice data transmitted from each of a plurality of terminals respectively used by a plurality of workers, each terminal for inputting utterances about work by each of the plurality of workers; and
transmit the text data to each terminal used by each worker.

7. The information processing apparatus of claim 6, wherein the circuitry is further configured to:
store the text data and the voice data in association in the memory;
transmit the text data and identification information of storage destination of the voice data to each terminal used by each worker; and
in response to a request for acquisition of the voice data based on the identification information from a particular terminal of the terminals, transmit to the particular terminal the voice data related to the identification information.

8. The information processing apparatus of claim 1, wherein the circuitry is further configured to:
register a schedule corresponding to each of a plurality of work targets; and
update the work implementation status information based on the work target and work content of the work that are identified and the schedule corresponding to the identified work target among the registered schedules.

9. An information processing system comprising:
a terminal for inputting utterance about work by a worker;
an information processing apparatus; and
a display terminal, wherein the information processing apparatus includes circuitry configured to:
register a schedule of the work;
identify a work target and work content of the work, based on voice data sent from the terminal;
update work implementation status information indicating work implementation status of the work stored in a memory based on the work target and work content of the work that are identified and the schedule corresponding to the work target;
measure an elapsed time of the work target and work content of the work that are identified; and
control to display the work implementation status of the work based on the work implementation status information on the display terminal connected through a network, wherein
in a case where the elapsed time of the work target and work content of the work that are identified exceeds a threshold allowable time, the circuitry transmits an alert indicating that the work target and work content of the work that are identified remains incomplete is transmitted to the terminal.

10. The information processing system of claim 9, wherein the circuitry is further configured to
update, of work implementation status information corresponding to a plurality of work targets, the work implementation status information corresponding to the work target of the work that is identified.

11. The information processing system of claim 9, wherein the circuitry is further configured to
identify the work target and work content of the work based on analysis result of the voice data and definition information that defines correspondence between the work target, the work content, and the analysis result.

12. An information processing method comprising:
registering a schedule of work;
identifying a work target and work content of the work, based on voice data sent from a terminal for inputting utterance about the work by a worker;
updating work implementation status information indicating work implementation status of the work stored in a memory based on the work target and work content of the work that are identified and the schedule corresponding to the work target;
measuring an elapsed time of the work target and work content of the work that are identified; and controlling to display the work implementation status of the work based on the work implementation status information on a display terminal connected through a network, wherein in a case where the elapsed time of the work target and work content of the work that are identified exceeds a threshold allowable time, the circuitry transmits an alert indicating that the work target and work content of the work that are identified remains incomplete is transmitted to the terminal.

13. The information processing method of claim 12, further comprising updating, of work implementation status information corresponding to a plurality of work targets, the work implementation status information corresponding to the work target of the work that is identified.

14. The information processing method of claim 12, further comprising identifying the work target and work content of the work based on analysis result of the voice data and definition information that defines correspondence between the work target, the work content, and the analysis result.

* * * * *